(12) United States Patent
Iyer et al.

(10) Patent No.: US 7,590,450 B2
(45) Date of Patent: Sep. 15, 2009

(54) FILTERED ELECTRICAL INTERCONNECT ASSEMBLY

(75) Inventors: Rajesh V. Iyer, Eden Prairie, MN (US); Shawn D. Knowles, Saint Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 339 days.

(21) Appl. No.: 11/343,174

(22) Filed: Jan. 30, 2006

(65) Prior Publication Data

US 2007/0179551 A1 Aug. 2, 2007

(51) Int. Cl.
*A61N 1/00* (2006.01)
(52) U.S. Cl. .............................. 607/36; 607/2; 361/302
(58) Field of Classification Search .................. 607/36, 607/37, 2, 5; 361/302–306
See application file for complete search history.

(56) References Cited

U.S. PATENT DOCUMENTS

| 5,620,476 | A | 4/1997 | Truex et al. |
| 5,683,435 | A | 11/1997 | Truex et al. |
| 5,782,891 | A | 7/1998 | Hassler et al. |
| 6,349,025 | B1 * | 2/2002 | Fraley et al. ................. 361/302 |
| 6,765,780 | B2 * | 7/2004 | Brendel et al. ............... 361/302 |
| 7,210,966 | B2 * | 5/2007 | Taylor et al. ........... 439/620.09 |
| 2005/0007718 | A1 * | 1/2005 | Stevenson et al. ........... 361/118 |
| 2005/0024837 | A1 | 2/2005 | Youker et al. |

OTHER PUBLICATIONS

Brian Davidson et al., MID Wide Band Helix Antenna for PDC Diversity, Prime Faraday Technology Watch, Feb. 2002.
Moulded Interconnect Devices, Prime Faraday Technology Watch, Feb. 2002, found on internet at http://www.primetechnologywatch.org.uk.

* cited by examiner

*Primary Examiner*—Leonardo Andújar

(57) ABSTRACT

An electronic module assembly for an implantable medical device includes a non-conductive block having an opening for accepting a feedthrough conductor. The block has opposite first and second ends and opposite first and second sides. A bond pad is located on the first end of the block for electrical connection to a feedthrough conductor, and the bond pad extends to the first side of the block to provide an electrical connection region there.

14 Claims, 6 Drawing Sheets

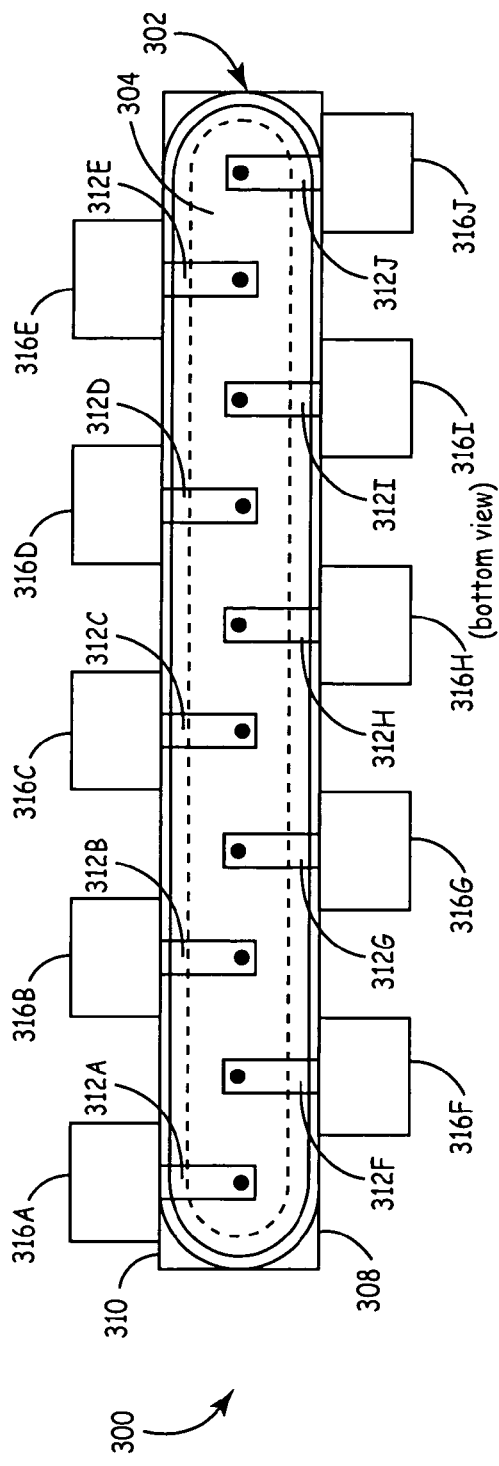
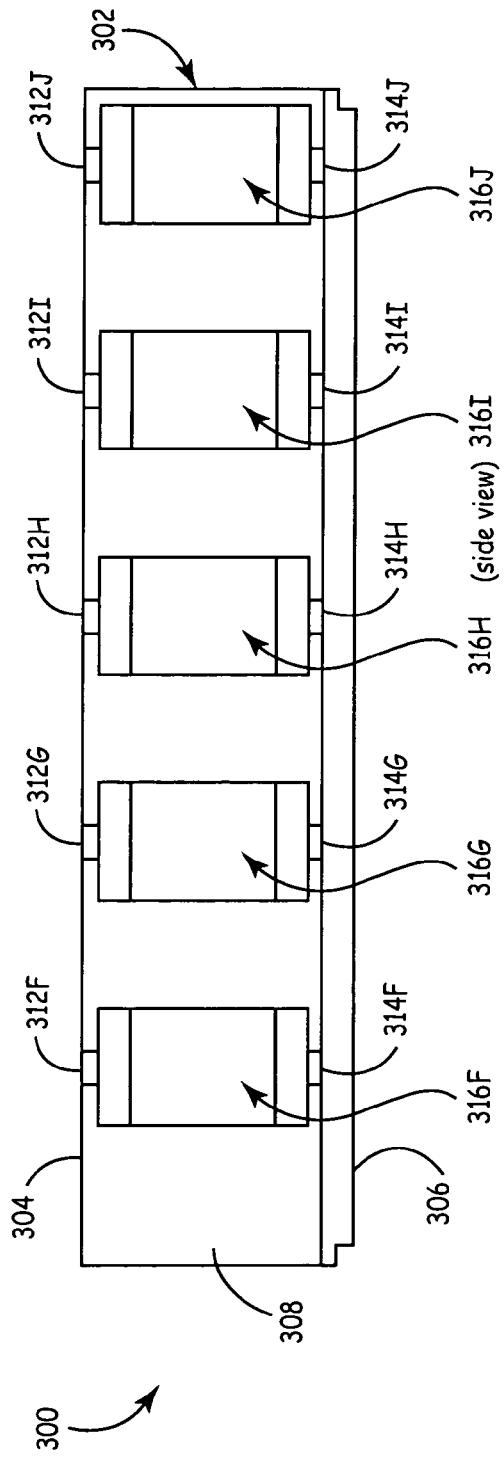

(bottom view)

(side view)

FILTERED ELECTRICAL INTERCONNECT ASSEMBLY

BACKGROUND OF THE INVENTION

The present invention relates to implantable medical devices. More particularly, the present invention relates to electrical interconnect assemblies having filtering capabilities.

Electrical feedthroughs provide a conductive path extending between the interior of a hermetically sealed container and a point outside the container. With typical feedthrough assemblies for implantable medical devices (IMDs), a connector module for attaching leads is connected to an exterior side of a unipolar or multipolar feedthrough, and an electronic module assembly (EMA) (also called a molded interconnect device) is connected to an interior side of the feedthrough. Filtering circuitry is often connected to the feedthrough assembly to minimize the introduction of undesired electromagnetic interference (EMI) into the device via the feedthrough assembly. However, known filtered feedthrough assemblies are often expensive and occupy excessive amounts of space. It is desirable to provide a filtered feedthrough assembly that is simple and easy to assemble, as well as one that is relatively compact in size.

BRIEF SUMMARY OF THE INVENTION

An electronic module assembly (EMA) has bond pads that extend from an end portion of an EMA body to one or both sides of the EMA body, where electrical connection regions are formed. Non-conductive protrusions can optionally be formed between adjacent electrical connection regions, and filtering components such as capacitors can be connected at the electrical connection regions.

BRIEF DESCRIPTION OF THE DRAWINGS

FIGS. 4 and 5 are bottom and side views, respectively, of a first alternative embodiment of a filtered EMA.

DETAILED DESCRIPTION

In general, the present invention provides a filtered electrical interconnect or feedthrough assembly for use with an implantable medical device (IMD). An electronic module assembly (EMA) is provided that has bond pads that extend from an end portion of an EMA body (where they can be electrically connected to feedthrough pins) to one or both sides of the EMA body (where electrical connection regions are formed). Filtering components, such as chip capacitors, can be connected to the electrical connection regions. Non-conductive protrusions can optionally be formed between adjacent electrical connection regions to provide high voltage (HV) isolation therebetween and facilitate alignment of capacitors mounted there during assembly. This provides a simple, compact and relatively inexpensive filtered electrical interconnect assembly that lends itself to easy fabrication.

Figure 1:
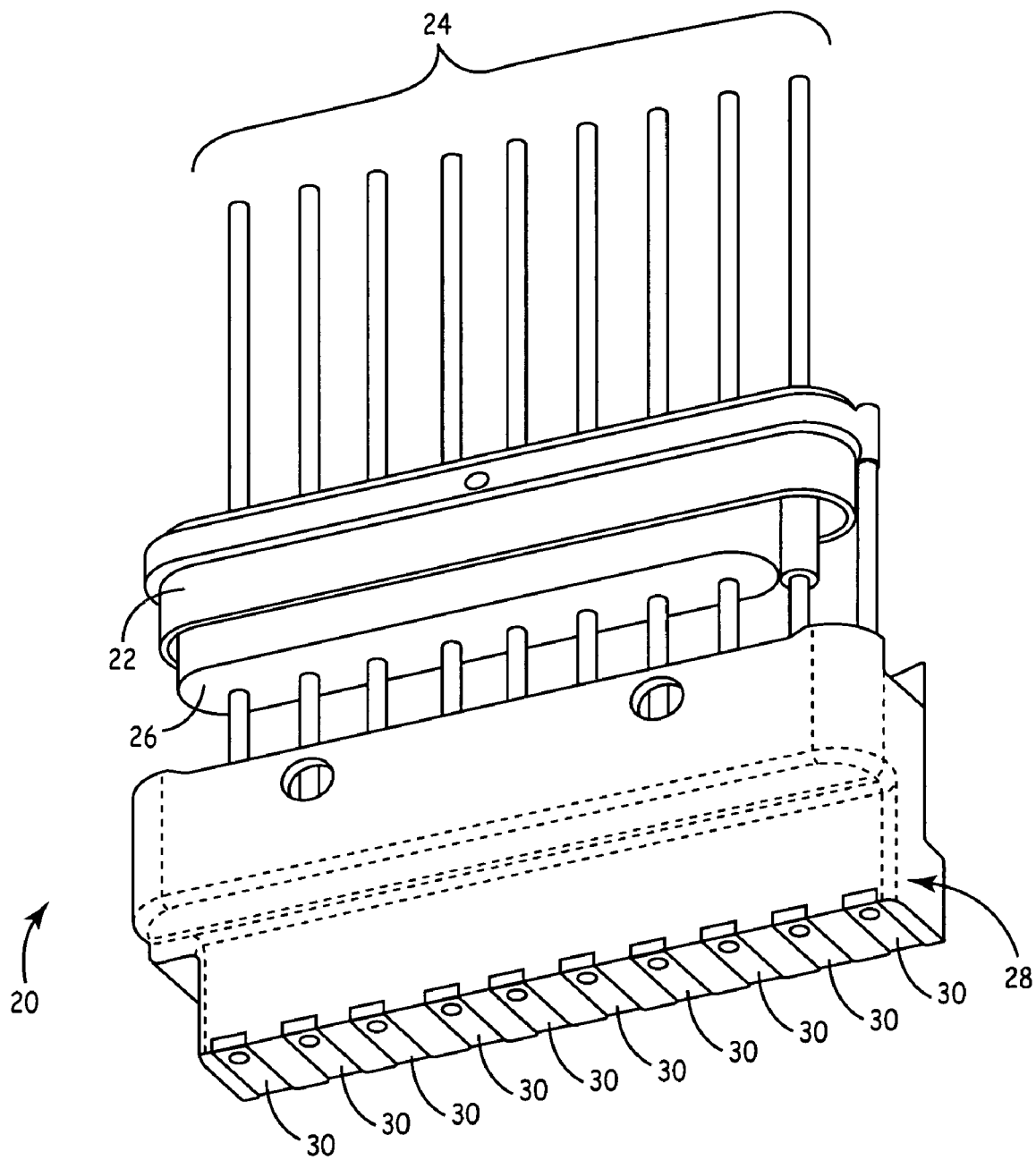
FIG. 1 is an exploded perspective view of a prior art filtered feedthrough assembly.

FIG. 1 is an exploded perspective view of a prior art filtered multipolar feedthrough assembly 20 for use with an IMD. The assembly 20 includes an electrically grounded ferrule 22 and an array of feedthrough pins 24 extending through the ferrule 22, with a non-conductive hermetic seal (not shown) formed between each of the feedthrough pins 24 and the ferrule 22. A monolithic discoidal capacitor assembly 26 is positioned around at least some of the feedthrough pins 24. The capacitor assembly 26 includes a number of discrete discoidal capacitors held together by a monolithic body, and each discrete capacitor of the assembly 26 is electrically connected between a feedthrough pin 24 and ground (i.e., to the ferrule 22) to provide low-pass electromagnetic interference (EMI) filtering. An EMA block 28 can be positioned over the feedthrough pin array 24 and the discoidal capacitor assembly 26. The EMA block 28 includes a number of bond pads 30 that can each be electrically connected to one of the feedthrough pins 24. The bond pads 30 are located solely at an end of the EMA block 28.

A problem with the prior art feedthrough assembly 20 is that the monolithic discoidal capacitor assembly 26 is expensive. Moreover, because each of the discrete discoidal capacitors is contained within a single monolithic body, the replacement of one discoidal capacitor requires the replacement of the entire assembly 26. This can lead to lower production yields and increased manufacturing costs.

Figure 2:
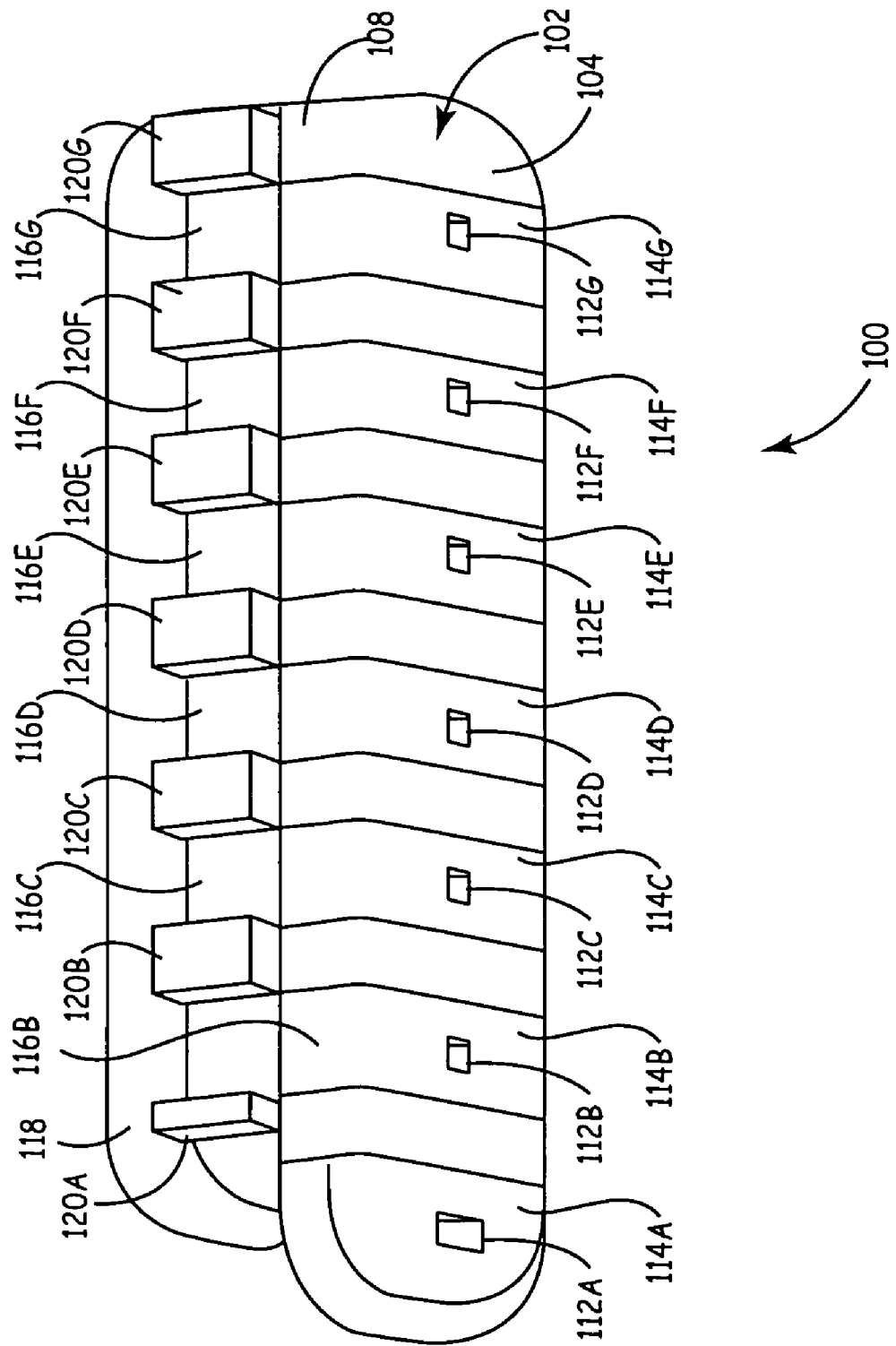
FIG. 2 is a perspective view of an electronic module assembly (EMA) according to the present invention.

FIG. 2 is a perspective view of an EMA block 100 according to the present invention. The EMA block 100 includes a non-conductive body 102 that has a first end 104 and an opposite second end 106 (not visible in FIG. 2), as well as a first side 108 and an opposite second side 110 (not visible in FIG. 2). A number of openings 112A-112G are defined through the body 102 between its first and second ends 104 and 106. The openings 112A-112G are capable of accepting feedthrough conductors, such as feedthrough pins.

Bond pads 114A-114G are formed on the body 102 of the EMA block 100, with one opening 112A-112G passing through each bond pad 114A-114G. Bond pads 114B-114G each extend from the first end 104 of the body 102 to the first side 108 of the body 102, forming a conductive path therebetween. Bond pads 114B-114G form electrical connection regions 116B-116G at the first side 108 to facilitate making electrical connections to wires, filter components, or other desired parts. The bond pads 114A-114G are formed of a conductive material, for example, titanium and nickel/gold.

A conductive trace 118 is formed at the first side 108 of the body 102 of the EMA block 100 adjacent to its second end 106. The conductive trace 118 is spaced from the bond pads 114A-114G, and extends along substantially the entire length of the body 102. The conductive trace 118 can be electrically connected to ground. It will be recognized that, in further embodiments, the unitary conductive trace 118 can comprise a number of discrete electrical traces each connected to ground.

Protrusions or raised portions 120A-120G extend from the first side 108 of the body 102 of the EMA block 100. Each protrusion 120A-120G is located, essentially, between adjacent electrical connection regions 116B-116G. The protrusions 120A-120G comprise a non-conductive material, and can be integrally formed with the body 102. The size and shape of each protrusion can be selected according to design considerations for the particular application, as will be recognized by those skilled in the art. The protrusions 120A-120G can function like a shield, to increase high voltage (HV) electrical isolation between locations on either side of a particular protrusion. This can be helpful where capacitors or other electrical components are located between adjacent protrusions 120A-120G. Moreover, the protrusions can facilitate alignment of components with respect to the electrical connection regions 116B-116F and the conductive trace 118, when those components are attached to the first side 108 of the body 102 of the EMA block 100.

Figure 3:
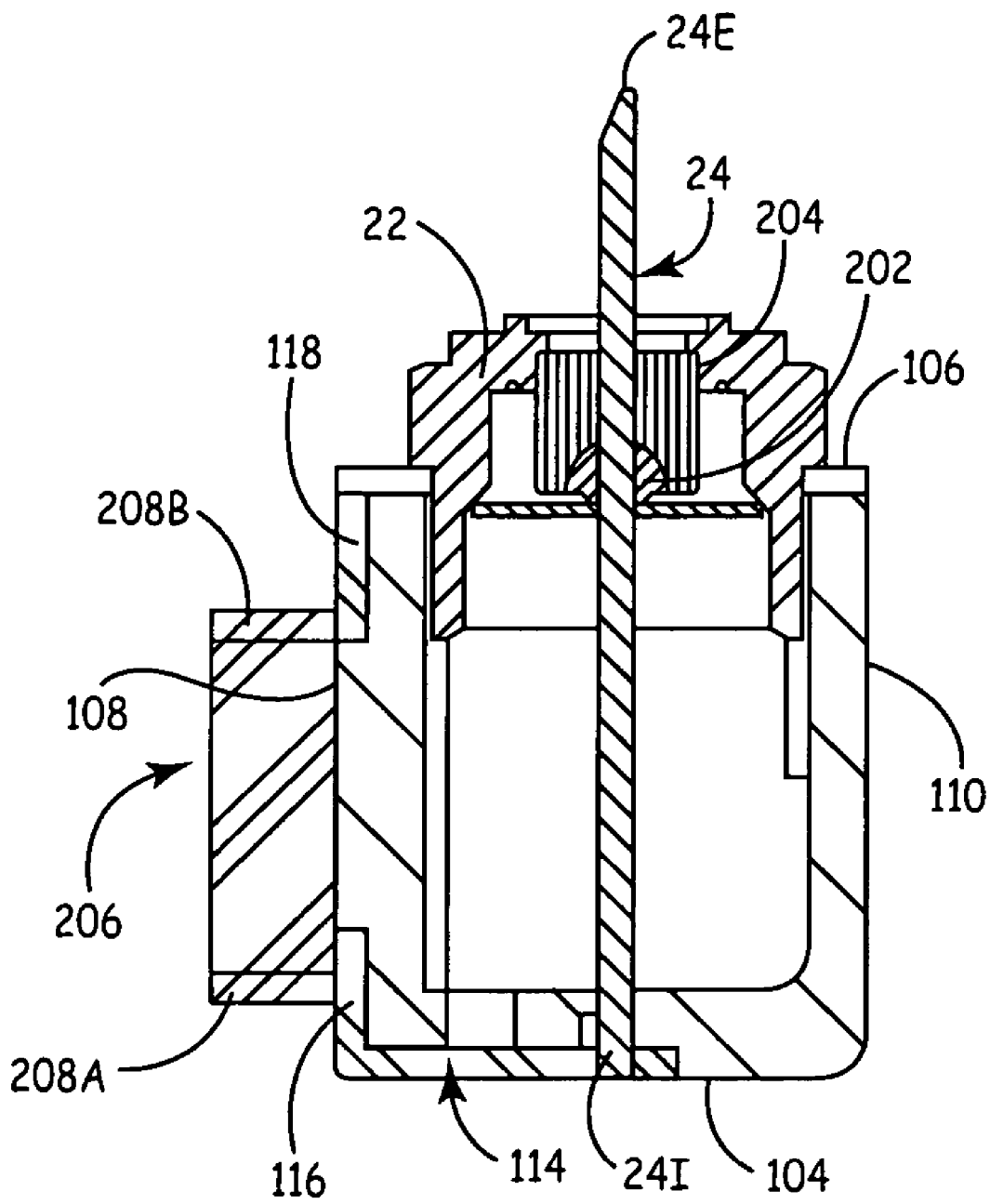
FIG. 3 is a cross-sectional view of a filtered feedthrough assembly utilizing the EMA of FIG. 2.

FIG. 3 is a cross-sectional view of a filtered feedthrough assembly 200.

The feedthrough assembly 200 includes a ferrule 22, a feedthrough pin 24 having an interior end $24_I$ and an exterior end $24_E$ that extends through the ferrule 22, a hermetic seal 202 disposed between the feedthrough pin 24 and the ferrule 22, and a conductive braze 204 applied to the feedthrough pin 24 adjacent to an interior side of the hermetic seal 202. It should be recognized that any type of conventional hermetic seal can be utilized in further embodiments.

An EMA bock 100, like that shown and described with respect to FIG. 2, is positioned at the interior side of the ferrule 22. A bond pad 114 is electrically connected to the interior end $24_I$ of the feedthrough pin 24. A conductive trace 118 is electrically grounded to the ferrule 22.

A chip capacitor 206 is mounted at the first side 108 of the EMA block 100, and has a first terminal 208A and a second terminal 208B. The particular value of the chip capacitor 206 can vary according to the particular application and the particular filtering desired. The first terminal 208A is electrically connected to the electrical connection region 116 of the bond pad 114, and the second terminal 208B is electrically connected to the conductive trace 118. Those electrical connections can be made with conductive adhesive, solder, or other suitable techniques.

The chip capacitor 206 is connected between the feedthrough pin 24 and ground to provide low-pass filtering, which attenuates undesired EMI that might otherwise be transmitted across the feedthrough assembly 200. In embodiments with protrusions at the first side 108 of the EMA block 100 (e.g., protrusions 120 in FIG. 2), the chip capacitor is located between adjacent protrusions. It should be recognized that other types of capacitors, as well as other types of electrical components can be connected to the electrical connection region 116 of the bond pad 114 and/or the conductive trace 118.

The arrangement of bond pads and capacitors on an EMA block according to the present invention can vary. The following are examples of embodiments utilizing alternative arrangements, though it should be recognized that further alternative embodiments are possible. FIGS. 4 and 5 are bottom and side views, respectively, of a first alternative embodiment of a filtered EMA block 300. The EMA block 300 has a body 302 with opposite first and second ends 304 and 306, respectively, and opposite first and second sides 308 and 310, respectively. Bond pads 312A-312E extend from the first end 304 of the body 302 to the second side 310 of the body 302, and bond pads 312F-312J extend from the first end 304 of the body 302 to the first side 308 of the body 302. The bond pads 312A-312J can be electrically connected to feedthrough pins (the locations for connections to feedthrough pins shown schematically as block dots). Conductive traces 314A-314E (not shown) are located on the second side 310 of the body 302, adjacent to its second end 306, and conductive traces 314F-314J are located on the first side 308 of the body 302, adjacent to its second end 306. The conductive traces 314A-314J can be electrically connected to ground.

Chip capacitors 316A-316E are attached to the second side 310 of the body 302 and chip capacitors 316F-316J are attached to the first side 308 of the body 302. As shown in FIG. 5, each capacitor 316F-316G is electrically connected between the bond pads 312F-312J and the conductive traces 314F-314J (and likewise for capacitors 316A-316E, not shown). In the embodiment shown in FIGS. 4 and 5, chip capacitors are staggered on either side of the EMA block body 302. This can facilitate positioning adjacent capacitors close together to reduce the size of the EMA block 300 in a lengthwise direction.

Figure 6:
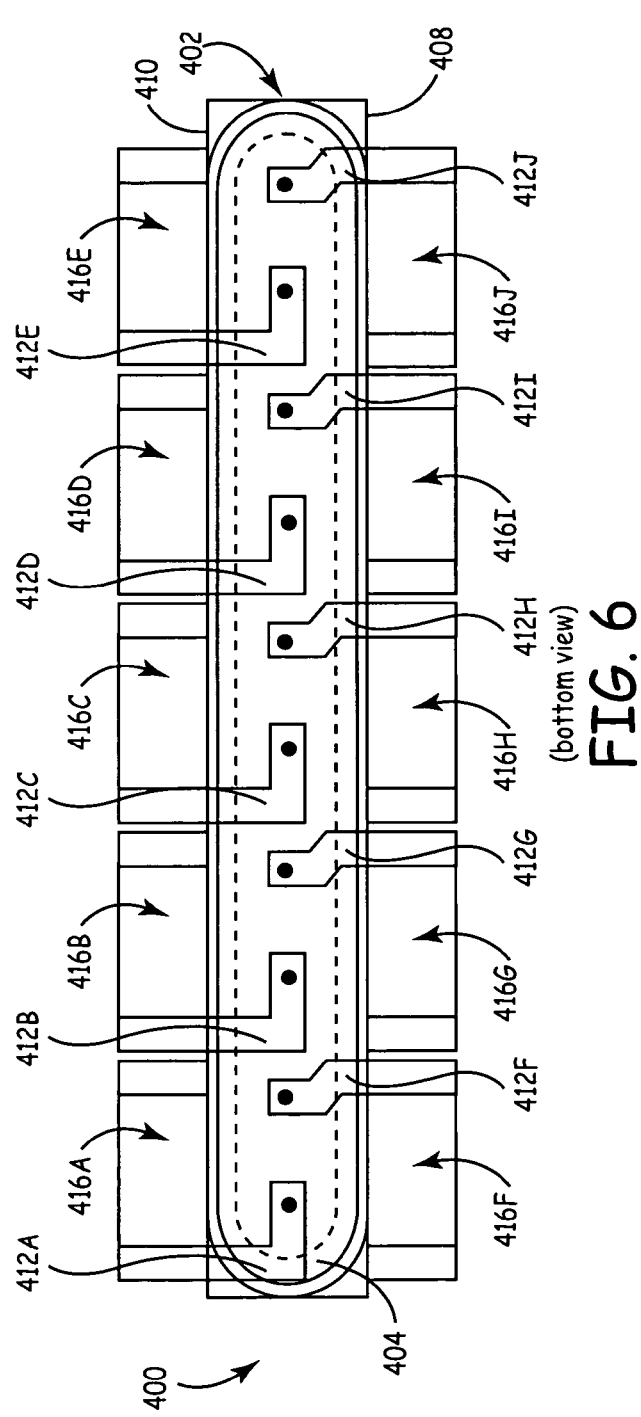
FIGS. 6 and 7 are bottom and side views, respectively, of a second alternative embodiment of a filtered EMA.
Figure 7:
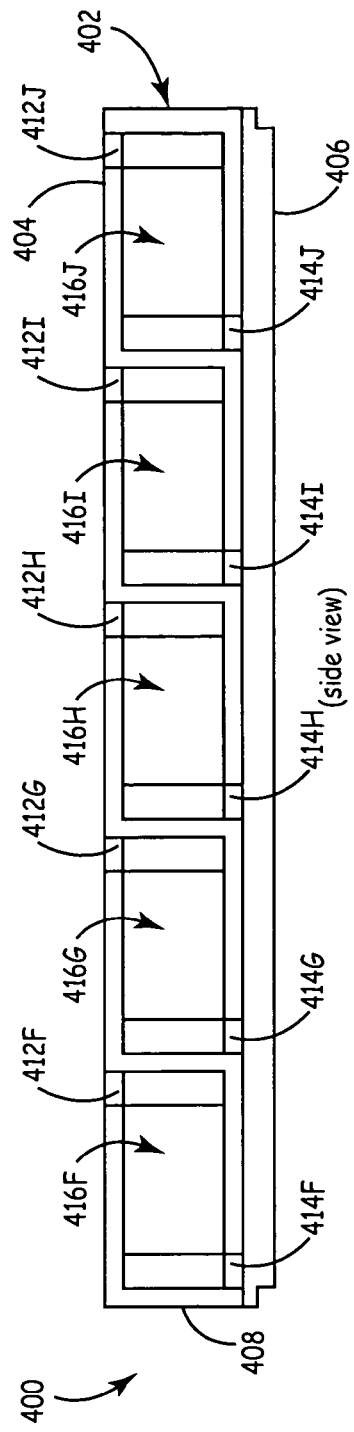

FIGS. 6 and 7 are bottom and side views, respectively, of a second alternative embodiment of a filtered EMA block 400, which is generally similar to EMA block 300 described above. The EMA block 400 has a body 402 with opposite first and second ends 404 and 406, respectively, and opposite first and second sides 408 and 410, respectively. Bond pads 412A-412E extend from the first end 404 of the body 402 to the second side 410 of the body 402, and bond pads 412F-412J extend from the first end 404 of the body 402 to the first side 408 of the body 402. Each bond pad 414-A-412J can be connected to a feedthrough pin. Conductive traces 414A-414E (not shown) are located on the second side 410 of the body 402, adjacent to its second end 406, and conductive traces 414F-414J are located on the first side 408 of the body 402, adjacent to its second end 406. The conductive traces 414A-414E are similar to the conductive traces 414F-414J, and each can be electrically connected to ground.

Chip capacitors 416A-416E are attached to the second side 410 of the body 402 and chip capacitors 416F-416J are attached to the first side 408 of the body 402. As shown in FIG. 7, each capacitor 416F-416G is electrically connected between the bond pads 412F-412J and the conductive traces 414F-414J (and likewise for capacitors 416A-416E, not shown). The capacitors 416A-416J, bond pads 412A-412J, and conductive traces 414A-414J of EMA block 400 have a different arrangement than EMA block 300 (FIGS. 4 and 5). EMA block 400 can facilitate positioning adjacent capacitors close together to reduce the height of the EMA block 300, and thereby reduce its size.

Figure 8:
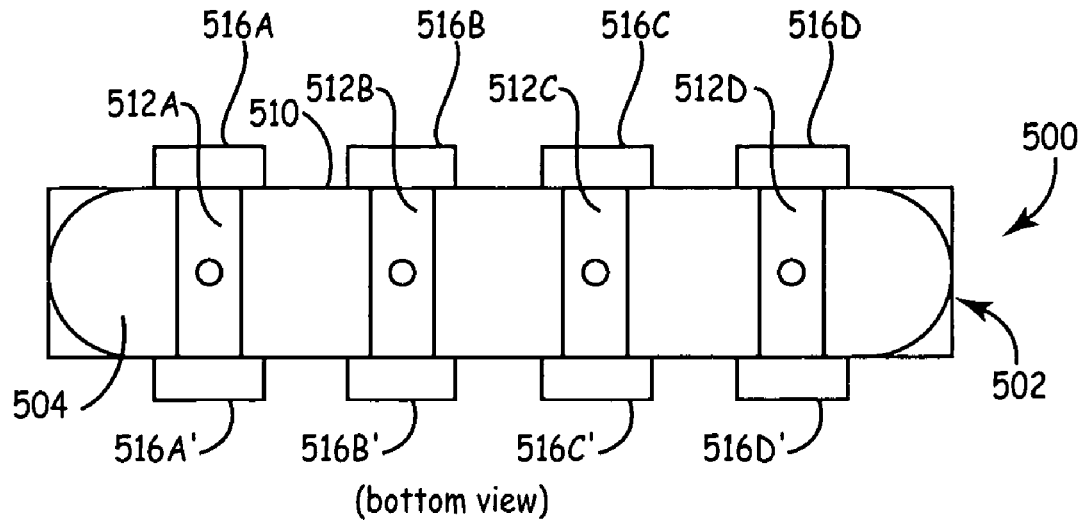
FIGS. 8 and 9 are bottom and side views, respectively, of a third alternative embodiment of a filtered EMA.
Figure 9:
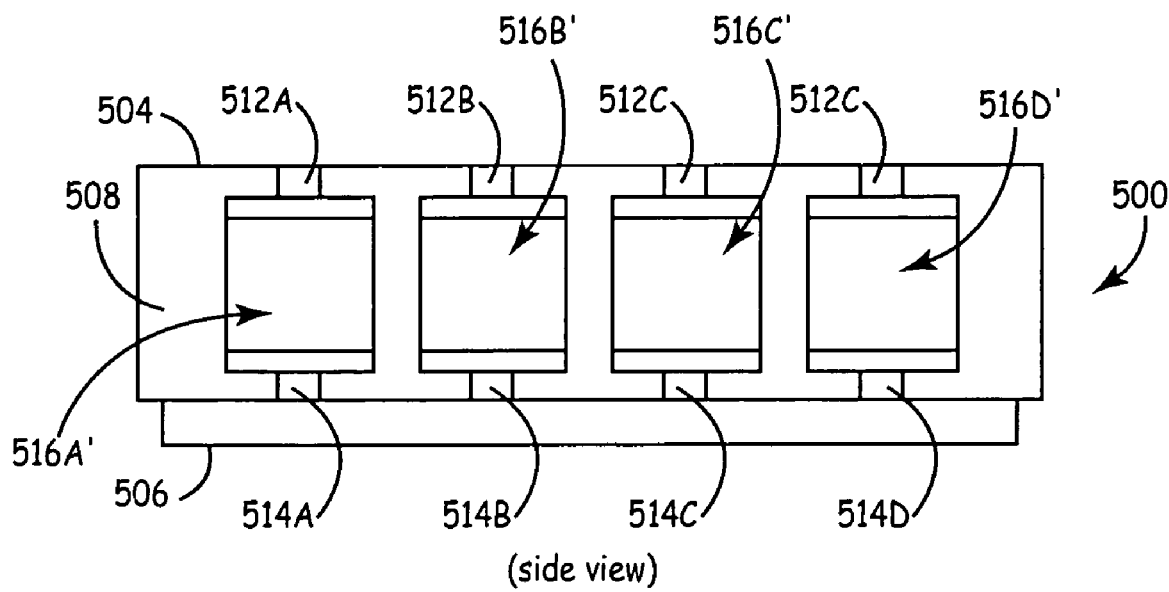

FIGS. 8 and 9 are bottom and side views, respectively, of a third alternative embodiment of a filtered EMA block 500, which is generally similar to EMA blocks 300 and 400 described above. The EMA block 500 has a body 502 with opposite first and second ends 504 and 506, respectively, and opposite first and second sides 508 and 510, respectively. Bond pads 512A-512D extend from the first end 504 of the body 502 to both first side 508 of the body 502 and the second side 510 of the body 502. Conductive traces 514A-514D are located on each side 508 and 510 of the body 502, adjacent to its second end 506 (while only the first side 508 of the body 502 is shown in FIG. 9, the second side 510 is identical). The conductive traces 514A-514D can be electrically connected to ground.

Chip capacitors 516A-516D are electrically connected between the bond pads 512A-512D and the conductive traces 514A-514D at the second side 510 of the body 502. Chip capacitors 516A'-516D' are electrically connected between the bond pads 512A-512D and the conductive traces 514A-514D at the first side 508 of the body 502. In this way, each bond pad 512A-512D is electrically connected to two grounded capacitors. Such a dual-capacitor filter system can provide increased capacitance filtering. Moreover, the use of such dual-capacitor filtering in can help maintain filtering capabilities in the event of a failure of one of the capacitors.

Thus, it will be recognized that the present invention provides an EMA block and filtered feedthrough assembly that is relatively inexpensive and easy to fabricate, and provides a relatively compact design. The interconnect structures of the present invention permit the use of chip capacitors for EMI filtering, which can provide benefits over monolithic discoidal capacitor assemblies for some applications.

Although the present invention has been described with reference to preferred embodiments, workers skilled in the art will recognize that changes may be made in form and detail without departing from the spirit and scope of the invention. For instance, the filtered electrical interconnect assembly of the present invention can be used in conjunction with either unipolar feedthrough assemblies or with multipolar feedthrough assemblies having any number of feedthrough conductors in any arrangement.

The invention claimed is:

1. An electronic module assembly for an implantable medical device, the assembly comprising:
   a non-conductive block having an opening for accepting a feedthrough conductor, wherein the block has opposite first and second ends and opposite first and second sides, and wherein the second end of the block is adapted for insertion into a portion of a ferrule; and
   a bond pad located on the first end of the block for electrical connection to a feedthrough conductor, wherein the bond pad extends to the first side of the block for providing a first electrical connection region at the first side of the block.

2. The assembly of claim 1 and further comprising:
   a chip capacitor that is electrically connected between the first electrical connection region and ground.

3. The assembly of claim 1, wherein the bond pad extends to the second side of the block for providing a second electrical connection region at the second side of the block.

4. The assembly of claim 3 and further comprising:
   a chip capacitor that is electrically connected between the second electrical connection region and ground.

5. The assembly of claim 1 and further comprising:
   a first raised portion located at the first side of the block.

6. The assembly of claim 5 and further comprising:
   a capacitor located adjacent to the first raised portion.

7. The assembly of claim 1 and further comprising:
   an extension portion of the block extending along the first end of the block, wherein the extension portion has an opening therethrough for accepting an antenna.

8. The assembly of claim 1 and further comprising:
   a noise filter circuit electrically connected to the first electrical connection region.

9. The assembly of claim 1, wherein the feedthrough conductor is a pin.

10. A feedthrough assembly for an implantable medical device, the assembly comprising:
    a ferrule;
    a feedthrough conductor extending through the ferrule;
    a hermetic seal between the ferrule and the feedthrough conductor; and
    an electronic module subassembly comprising:
       a non-conductive block having an opening extending between opposite first and second ends of the block for accepting the feedthrough conductor, wherein the block further defines opposite first and second sides; and
       a bond pad located on the first end of the block for electrical connection to the feedthrough conductor, wherein the bond pad extends to the first side of the block for providing a first electrical connection region at the first side of the block.

11. The assembly of claim 10 and further comprising:
    a chip capacitor electrically connected between the first electrical connection region and ground.

12. The assembly of claim 10, wherein the bond pad extends to the second side of the block for providing a second electrical connection region at the second side of the block.

13. The assembly of claim 12 and further comprising:
    a chip capacitor that is electrically connected between the second electrical connection region and ground.

14. The assembly of claim 10 and further comprising:
    a first raised portion located at the first side of the block.

* * * * *

UNITED STATES PATENT AND TRADEMARK OFFICE
CERTIFICATE OF CORRECTION

PATENT NO. : 7,590,450 B2  Page 1 of 1
APPLICATION NO. : 11/343174
DATED : September 15, 2009
INVENTOR(S) : Iyer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 567 days.

Signed and Sealed this

Twenty-first Day of September, 2010

David J. Kappos
*Director of the United States Patent and Trademark Office*